(12) United States Patent
Park et al.

(10) Patent No.: US 11,703,492 B2
(45) Date of Patent: Jul. 18, 2023

(54) GAS-DETECTING APPARATUS

(71) Applicant: HONEYWELL INTERNATIONAL INC., Morris Plains, NJ (US)

(72) Inventors: Jun-Seong Park, Seoul (KR); Je-Phil Ahn, Seoul (KR); Joung-Ho Lim, Seoul (KR); Jae-Jin Lee, Seoul (KR)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 392 days.

(21) Appl. No.: 16/955,151

(22) PCT Filed: Jan. 10, 2018

(86) PCT No.: PCT/KR2018/000468
§ 371 (c)(1),
(2) Date: Jun. 18, 2020

(87) PCT Pub. No.: WO2019/139183
PCT Pub. Date: Jul. 18, 2019

(65) Prior Publication Data
US 2020/0386732 A1 Dec. 10, 2020

(51) Int. Cl.
*G01N 33/00* (2006.01)
*G01N 1/24* (2006.01)
(Continued)

(52) U.S. Cl.
CPC .......... *G01N 33/0065* (2013.01); *G01F 1/48* (2013.01); *G01N 1/24* (2013.01); *G01N 1/34* (2013.01); *H01L 21/67017* (2013.01)

(58) Field of Classification Search
None
See application file for complete search history.

(56) References Cited

U.S. PATENT DOCUMENTS 6,383,354 B1   5/2002  Kurokawa et al.
6,792,794 B2   9/2004  Bonne et al.
(Continued)

FOREIGN PATENT DOCUMENTS

CN   101369514 A   2/2009
CN   101622530 A   1/2010
(Continued)

OTHER PUBLICATIONS

International Search Report and Written Opinion for International Patent Application No. PCT/KR2018/000468 dated Oct. 5, 2018, 9 pages.

(Continued)

*Primary Examiner* — Daniel S Larkin
(74) *Attorney, Agent, or Firm* — Alston & Bird LLP

(57) ABSTRACT

A gas-detecting apparatus includes a pump module connected to a first input and a second input to intake air, a sensor module including at least one unit sensor configured to output a sensing signal in response to gas present in the air, and a control module configured to detect the gas using the sensing signal. The control module controls the pump module to intake second air by opening the second input when gas is detected in first air introduced through the first input, and determines that gas is detected when a concentration of gas detected in the second air is lower than a concentration of gas detected in the first air.

20 Claims, 11 Drawing Sheets

(51) Int. Cl.
  *G01N 1/34* (2006.01)
  *G01F 1/48* (2006.01)
  *H01L 21/67* (2006.01)

(56) References Cited

U.S. PATENT DOCUMENTS

| | | |
|---|---|---|
| 2004/0060346 A1 | 4/2004 | Bonne et al. |
| 2004/0200460 A1 | 10/2004 | Mitani et al. |
| 2005/0026268 A1 | 2/2005 | Apajalahti et al. |
| 2008/0202212 A1 | 8/2008 | Liepert |
| 2015/0226129 A1 | 8/2015 | Byrd et al. |
| 2016/0054215 A1 | 2/2016 | Williamson |

FOREIGN PATENT DOCUMENTS

| | | | |
|---|---|---|---|
| CN | 102460028 A | | 5/2012 |
| CN | 204288475 U | | 4/2015 |
| DE | 11 2008 002 706 | * | 8/2013 |
| EP | 1683998 A2 | | 7/2006 |
| JP | 10-267885 A | | 10/1998 |
| JP | 2007-147293 A | | 6/2007 |
| JP | 2015-105861 A | | 6/2015 |
| KR | 10-2010-0109015 A | | 10/2010 |
| KR | 10-1096535 B1 | | 12/2011 |
| KR | 10-2016-0107650 A | | 9/2016 |
| KR | 10-1695651 B1 | | 1/2017 |

OTHER PUBLICATIONS

International Search Report of the International Searching Authority for PCT/KR2018/000468 dated Oct. 5, 2018.
English Translation of CN Office Action dated Feb. 2, 2023 for CN Application No. 201880085787.
CN Office Action dated Feb. 2, 2023 for CN Application No. 201880085787, 6 page(s).
English Translation of CN Office Action dated Feb. 2, 2023 for CN Application No. 201880085787, 9 page(s).
CN Notice of Allowance dated Apr. 28, 2023 for CN Application No. 201880085787, 2 page(s).
English translation of CN Notice of Allowance dated Apr. 28, 2023 for CN Application No. 201880085787, 2 page(s).

* cited by examiner

GAS-DETECTING APPARATUS

TECHNICAL FIELD

The present inventive concept relates to a gas-detecting apparatus.

BACKGROUND ART

Various gases are used in semiconductor processing lines and in industrial sites, and thus, gas-detecting apparatuses are commonly used to prevent large scale accidents caused by gas leaks. Such a gas-detecting apparatus may detect a gas leaked from a chamber in which a semiconductor process is performed or a gas pipe or valve connected to the chamber, or determine whether or not a gas leak has occurred in an industrial site. When such a gas-detecting apparatus detects a gas leak and sounds an alarm, a gas pipe connected to the chamber is shut off or operations of the chamber are stopped. Therefore, it is important that the gas-detecting apparatus accurately determines whether a gas leak has occurred.

DISCLOSURE OF INVENTION

Technical Problem

An aspect of the present inventive concept may provide a gas-detecting apparatus accurately detecting a gas leak.

Solution to Problem

According to an aspect of the present inventive concept, a gas-detecting apparatus may include a pump module connected to a first input and a second input to intake air, a sensor module including at least one unit sensor configured to output a sensing signal in response to gas, such as a leaked or sensed gas, present in the air, and a control module configured to detect the gas using the sensing signal. The control module may control the pump module to intake second air by opening the second input when gas, such as a leaked or sensed gas, is detected in first air introduced through the first input, and determine that gas, such as a leaked or sensed gas, is detected when a concentration of gas detected in the second air is lower than a concentration of gas, such as a leaked or sensed gas, detected in the first air.

According to another aspect of the present inventive concept, a gas-detecting apparatus may include a sensor module including at least one unit sensor configured to output a sensing signal in response to gas, such as a leaked or sensed gas, a pump module configured to supply at least one of external air, having been intaken, through a first input and circulating air intaken through a second input to the sensor module, a control module configured to detect the gas, such as a leaked or sensed gas, using the sensing signal, and a gas filter connected between an output of the pump module and an input of the sensor module and configured to generate the cir-culating air by filtering the external air passing through the sensor module. The control module may supply the circulating air to the sensor module by closing the first input and opening the second input when gas, such as a leaked or sensed gas, is detected in the external air, and determine that gas, such as a leaked or sensed gas, is detected when a concentration of gas detected in the circulating air is lower than a concentration of gas detected in the external air.

According to another aspect of the present inventive concept, a gas-detecting apparatus may include a pump module configured to intake air, a sensor module configured to detect gas, such as a leaked or sensed gas, present in the air at a first point in time and a second point in time coming after the first point in time and output a sensing signal, and a control module configured to determine whether or not to output an alarm by setting a first threshold value and a second threshold value greater than the first threshold value, comparing the sensing signal with the first threshold value at the first point in time, and comparing the sensing signal with the second threshold value at the second point in time. The control module may output the alarm when the sensing signal decreases during a predetermined verification time defined between the first point in time and the second point in time.

Advantageous Effects of Invention

According to an example embodiment of the present inventive concept, when gas leakage is suspected by a sensing signal generated in response to a gas, such as a leaked or sensed gas, a gas detecting apparatus can judge whether or not the sensing signal is decreased by intaking an air. Therefore, the gas-detecting apparatus prevent malfunction of an alarm due to noise such as an electrical signal or an RF signal. Furthermore, it is possible to efficiently operate a chamber or a gas pipe connected to the gas detecting apparatus.

MODE FOR THE INVENTION

Hereinafter, semiconductor devices according to example embodiments of the present inventive concept will be described with reference to the accompanying drawings.

Figure 1:
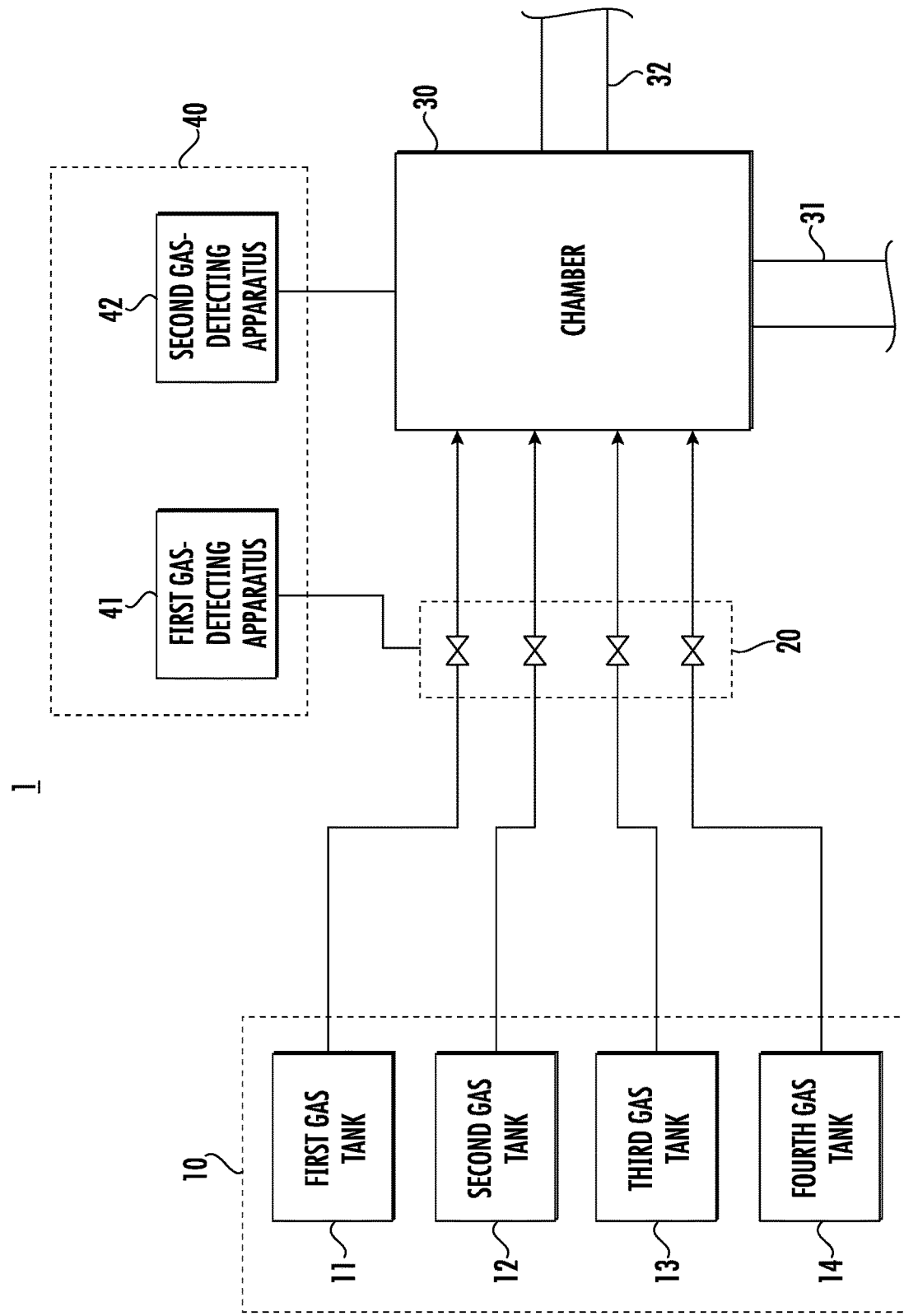
FIG. 1 is a simplified diagram of a processing facility including a gas-detecting apparatus according to an example embodiment of the present inventive concept.

FIG. 1 is a simplified diagram of a processing facility including a gas-detecting apparatus according to an example embodiment of the present inventive concept.

Referring to FIG. 1, a processing facility 1 according to an example embodiment of the present inventive concept may include a gas source 10, valves 20, a chamber 30, and a gas-detecting apparatus 40. The chamber 30 may receive a gas from the gas source 10 to proceed with a predetermined production process. In some example embodiments, the chamber 30 may be a semiconductor processing apparatus in which a semiconductor process, such as an etching process, a deposition process, a photolithography process, or a cleaning process, is performed. The chamber 30 may be connected to transportation paths 31 and 32 transporting a substrate on which the semiconductor process is performed, and may receive gases required for the semiconductor process from the gas source 10.

The gas source 10 may include first to fourth gas tanks 11 to 14 respectively containing different gases. Although the gas source 10 has four gas tanks 11 to 14 in total, in the example embodiment illustrated in FIG. 1, the present inventive concept is not limited thereto. It is obvious that fewer or more gas tanks may be included in the gas source 10. Gases contained in the first to fourth gas tanks 11 to 14 may be supplied to the chamber 30 by operations of valves 20.

In the example embodiment illustrated in FIG. 1, the gas-detecting apparatus 40 may include a first gas-detecting apparatus 41 and a second gas-detecting apparatus 42. The first gas-detecting apparatus 41 may be connected to valves 20 to detect whether or not the gas supplied from the first to fourth gas tanks 11 to 14 to valves 20 has leaked. Meanwhile, the second gas-detecting apparatus 42 may be connected to the chamber 30 to measure a concentration of each of various gases contained in the chamber 30 or to determine whether or not the gas has leaked out of the chamber 30. As necessary, a greater number of gas-detecting apparatuses may be connected to a gas-supplying path, the chamber 30, or the like.

Figure 2:
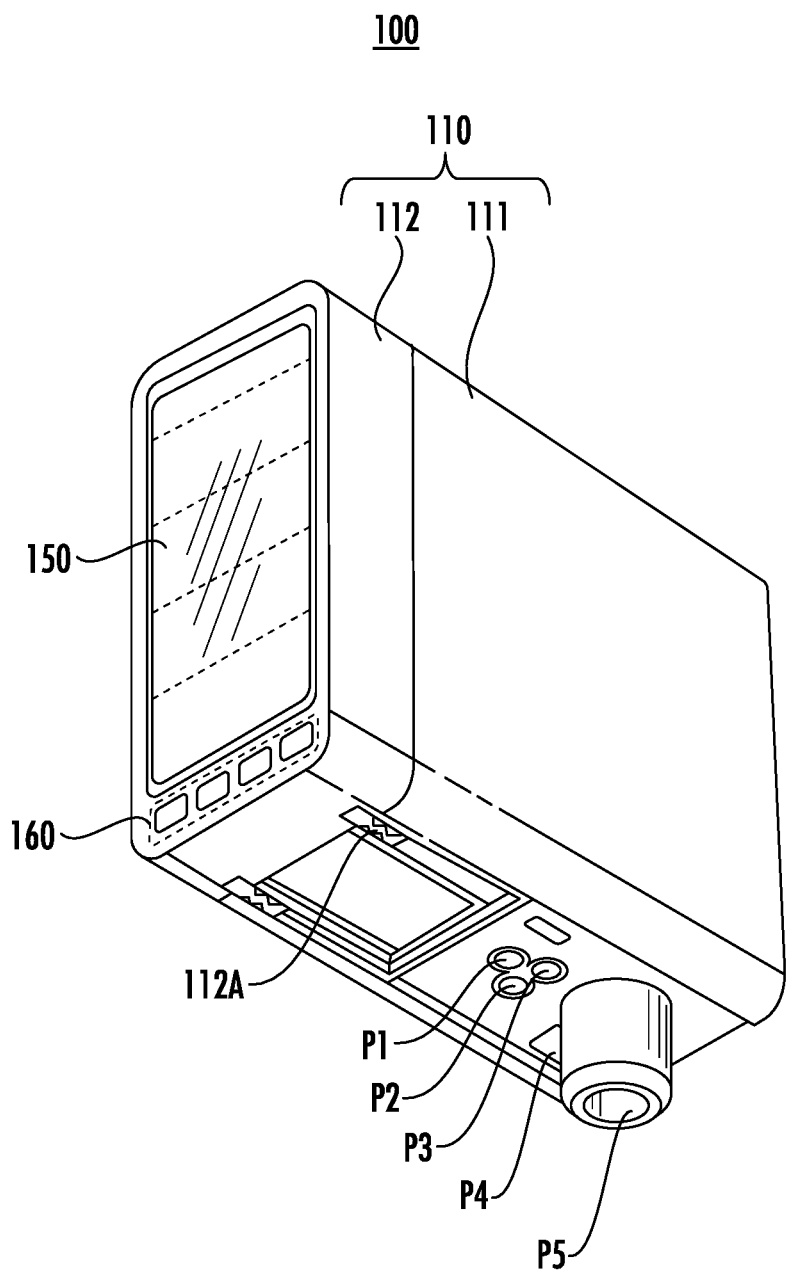
FIGS. 2 and 3 are diagrams illustrating external features of a gas-detecting apparatus according to an example embodiment of the present inventive concept.
Figure 3:
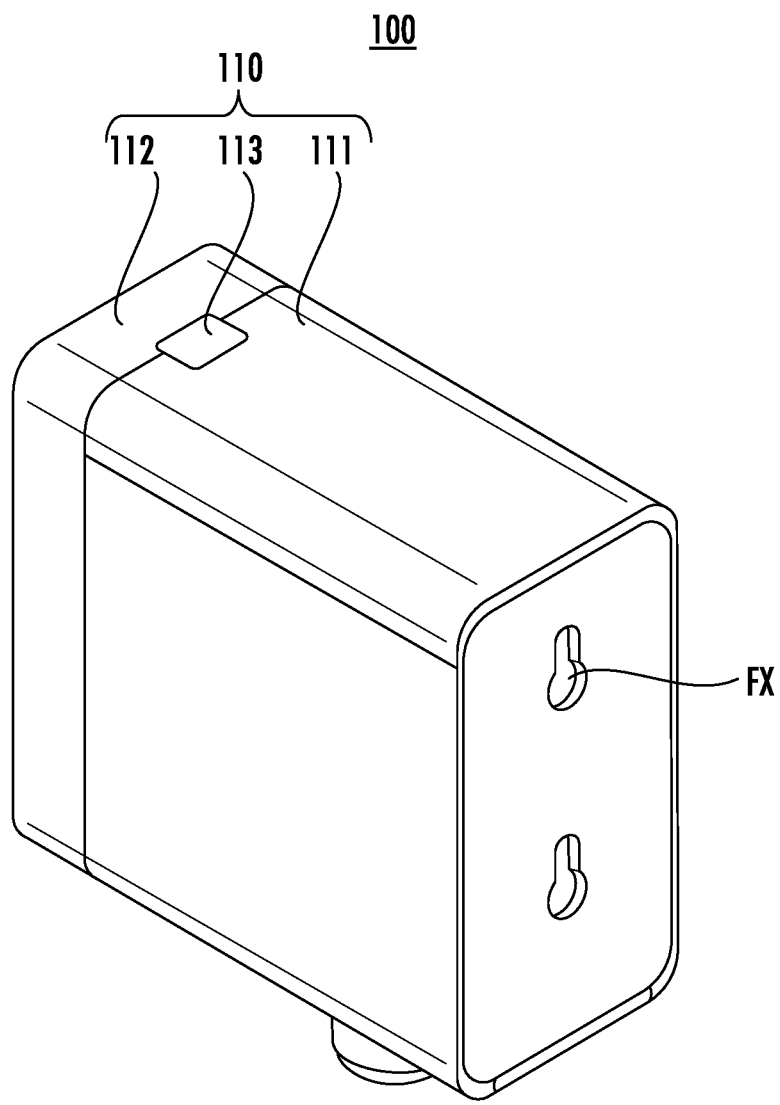

FIGS. 2 and 3 are diagrams illustrating external features of a gas-detecting apparatus according to an example embodiment of the present inventive concept.

First, referring to FIG. 2, a gas-detecting apparatus 100 according to the example embodiment of the present inventive concept may include a case 110, a display 150, and an input 160. The case 110 may accommodate a pump module that intakes and discharges air to detect a gas, a sensor module sensing the gas included in the air intaken by the pump module, and a control module controlling overall operations of the gas-detecting apparatus 100.

The case 110 may include a body 111 and a cover 112 combined with the body 111. The cover 112 may be disposed on a front side of the case 110. In some example embodiments, the display 150 and the input 160 may be disposed on the cover 112. The input 160 may include a plurality of mechanical input keys, or a touch screen integrated with the display 150. In some example embodiments, the cover 112 may be combined with the body 111 by a hinge 113 disposed on one surface of the body 111 and the cover 112. The cover 112 may be rotated with respect to the hinge 113 to expose an inside of the body 111.

Referring to FIG. 2, the body 111 and the cover 112 according to the example embodiment of the present inventive concept may be engaged together by an engagement member 112A. The engagement member 112A may be formed on a surface of the cover 112 to combine and engage the body 111 and the cover 112 and prevent the cover 112 from opening while the gas-detecting apparatus 100 is operated.

Meanwhile, a plurality of ports P1 to P5 may be disposed on a lower surface of the case 110. In some example embodiments, the first port P1 and the second port P2 may be intake ports through which air is introduced, and the third port P3 may be an exhaust port through which the air is discharged. The air introduced through the first port P1 or the second port P2 by the operations of the pump module may be discharged through the third port P3 via the sensor module installed inside the case 110. The amount of air introduced through the first port P1 or the second port P2 to be discharged through the third port P3 may be determined by the pump module installed inside the case 110.

According to the example embodiment of the present inventive concept, the first port P1 and the second port P2 may be connected to different spaces. In some example embodiments, as described above with reference to FIG. 1, the first port P1 may be connected to a space such as the chamber 30 where a gas leak is determined, and the second port P2 may be connected to a general air tank that does not contain a gas to be determined for leakage or to a pipe into which external air is intaken. Accordingly, when a gas leak is suspected, an alarm may not be immediately output in order to verify whether or not gas has actually leaked.

Meanwhile, the fourth port P4 may be a Power-over-Ethernet (PoE) port. The gas-detecting apparatus 100 may communicate with external devices and receive power required to drive itself, through the fourth port P4. The fifth port P5 may be a cable gland through which power is supplied from an external device or a signal is input from an external controller.

Referring to FIG. 3, the gas-detecting apparatus 100 according to the example embodiment of the present inventive concept may include a fixing member FX disposed on a rear surface of the case 110. The fixing member FX may include a hole formed to a predetermined depth in the rear surface of the case 110. A user may install a ring or the like protruding outwardly from a wall or a device in a space in which the gas-detecting apparatus 100 is to be installed, and fix the gas-detecting apparatus 100 by inserting the ring into the fixing member FX. The gas-detecting apparatus 100 may intake and discharge air through the first to third ports P1 to P3 disposed on the lower surface of the case 110, in a state of being fixed by the fixing member FX.

Figure 4:
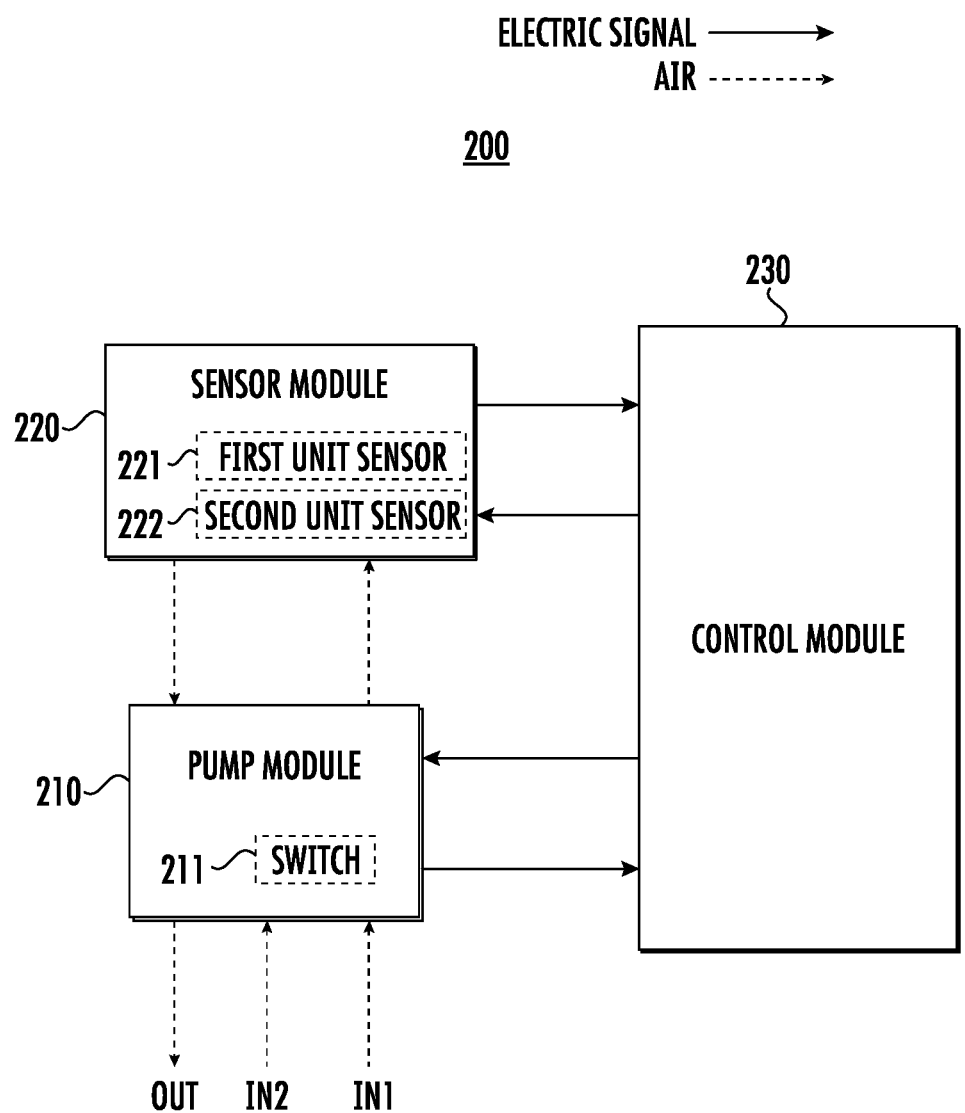
FIGS. 4 and 5 are simplified block diagrams illustrating gas-detecting apparatuses according to example embodiments of the present inventive concept.
Figure 5:
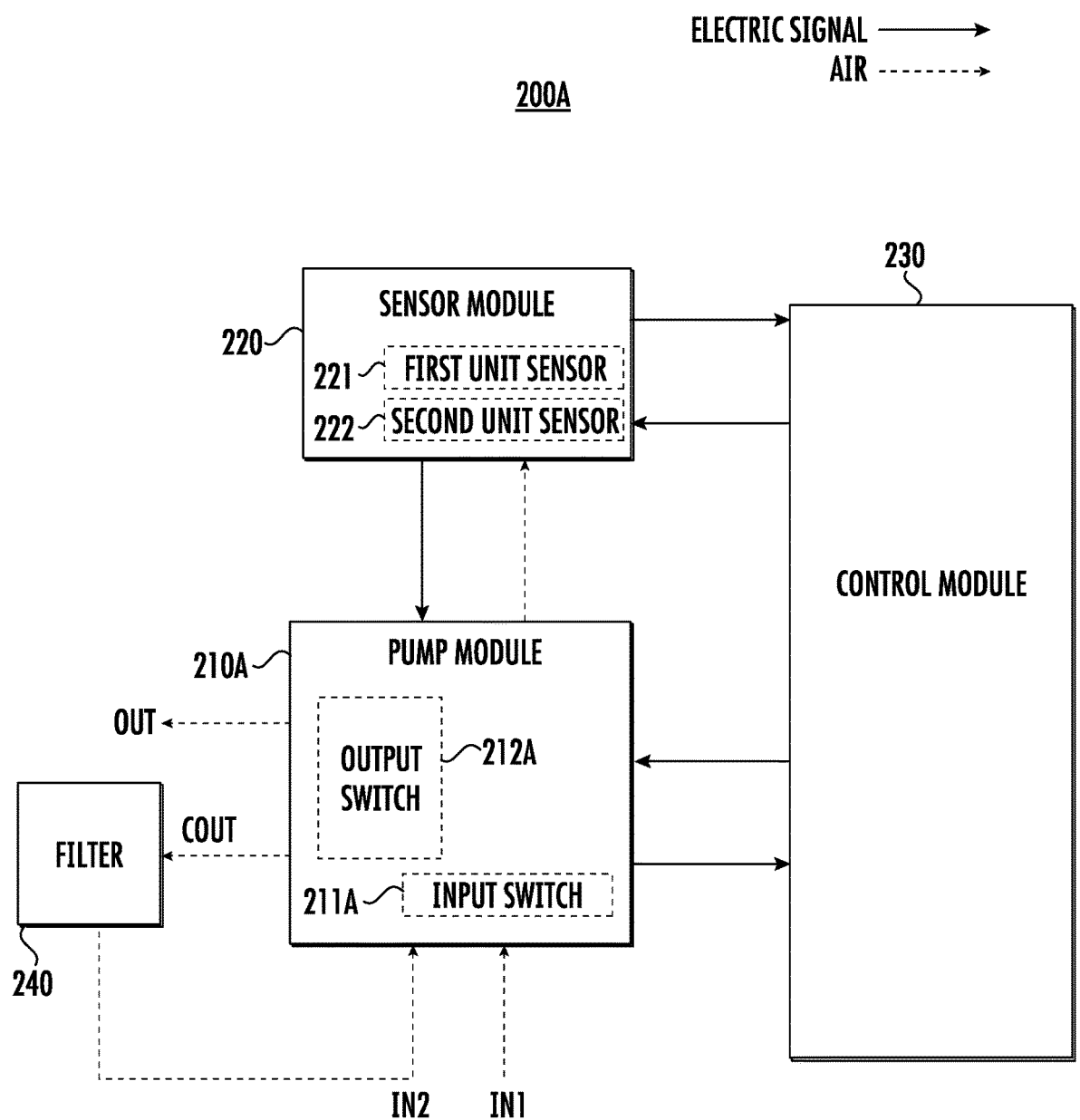

FIGS. 4 and 5 are simplified block diagrams illustrating gas-detecting apparatuses according to example embodiments of the present inventive concept.

Referring to FIG. 4, a gas-detecting apparatus 200 according to an example embodiment of the present inventive concept may include a pump module 210, a sensor module 220, and a control module 230. The pump module 210 may include a pump drawing in air to be supplied to the sensor module 220, a flow rate sensor measuring the amount of the air intaken by the pump, and a microtube providing a flow path of the air. The pump module 210 may be connected to ports disposed on a case of the gas-detecting apparatus 200 to intake and discharge air.

According to the example embodiment of the present inventive concept, the pump module 210 may be connected to two inputs IN1 and IN2 and one output OUT. The first input IN1 and the second input IN2 may be connected to different spaces via different pipes, respectively. In some example embodiments, the first input IN1 may be connected to a space in which a gas to be detected is used, and the second input IN2 may be connected to a space which does not contain the gas to be detected. For example, the second input IN2 may be connected to an air tank in which general air is stored, or to an outdoor space.

The pump module 210 may include a switch 211 selectively opening and closing each of the first input IN1 and the second input IN2. In some example embodiments, the switch 211 may be implemented as a solenoid valve, and the control module 230 may control operations of the switch 211. That is, the control module 230 may open and close each of the first input IN1 and the second input IN2 by controlling the switch 211.

The sensor module 220 may include a plurality of unit sensors 221 and 222 provided to detect gases included in the air that the pump module 210 intakes and supplies. Although the sensor module 220 includes the first and second unit sensors 221 and 222 in the example embodiment illustrated in FIG. 4, the number of the unit sensors 221 and 222 included in the sensor module 220 may be variously modified. The unit sensors 221 and 222 may output a sensing signal in response to different kinds of gases.

The control module 230 may supply power to operate the pump module 210 and the sensor module 220, and control the operations of the pump module 210 and the sensor module 220. The control module 230 may include a controller and a power supply circuit. The control module 230 may analyze the sensing signal output by the sensor module 220 to display a type and concentration of a gas present in the space connected to the first input IN1 on a display, or monitor a state of operations of the pump module 210 and the sensor module 220 to display whether or not a failure has occurred on the display.

The control module 230 may output an alarm when a magnitude of the sensing signal output by the sensor module 220 is greater than a predetermined threshold value. The alarm may be output on the display or as a specific audio signal. When a gas leak or the like occurs in the space connected to the first input IN1, a gas concentration may increase regardless of the intention of an operator, resulting in an increase in the magnitude of the sensing signal output by the sensor module 220.

When the magnitude of the sensing signal increases and exceeds a first threshold value, the control module 230 may close the first input IN1 and open the second input IN2 by using the switch 211, to intake air from the space in which the gas is not present. When the magnitude of the sensing signal decreases while the second input IN2 is open, the control module 230 may determine that an increase in the magnitude of the sensing signal is not caused by device failure or noise interference. Accordingly, the control module 230 may open the first input IN1 and close the second input IN2, and finally output an alarm when the magnitude of the sensing signal increases to (or above) a second threshold value, greater than the first threshold value.

Referring to FIG. 5, a gas-detecting apparatus 200A according to an example embodiment of the present inventive concept may include a pump module 210A, a sensor module 220, and a control module 230. In the gas-detecting apparatus 200A according to the example embodiment illustrated in FIG. 5, features of the sensor module 220 and the control module 230 may be similar to those in the gas-detecting apparatus 200 according to the example embodiment illustrated in FIG. 4.

The gas-detecting apparatus 200A according to the example embodiment illustrated in FIG. 5 may further include a gas filter 240. In some example embodiments, the gas filter 240 may be connected between the pump module 210A and the sensor module 220, to filter gas present in air flowing from the pump module 210A to the sensor module 220.

The pump module 210A may intake and discharge air through a first input IN1, a second input IN2, an output OUT, and a circulation output COUT. In some example embodiments, the pump module 210A may intake external air through the first input IN1. When the external air, having been intaken, passes through the sensor module 220, the pump module 210A may discharge the external air through the output OUT. The external air may be the air intaken through the first input IN1, from a space in which a gas leak is detected.

In addition, the pump module 210A may supply the external air passing through the sensor module 220 to the gas filter 240 by closing the first input IN1, the output OUT, and opening the circulation output COUT, as necessary. The gas filter 240 may filter the external air to generate circulating air, and the circulating air may be intaken to the second input IN2 of the pump module 210A and transmitted again to the sensor module 220.

When it is not necessary to determine whether or not a gas leak has occurred, the pump module 210A may intake the external air through the first input IN1 to be transmitted to the sensor module 220, and the external air passing through the sensor module 220 may be discharged through the output OUT. The sensor module 220 may generate a sensing signal in response to gas present in the air, and the control module 230 may determine whether or not a gas leak has occurred, according to the magnitude of the sensing signal.

For example, when the magnitude of the sensing signal increases and becomes greater than a first threshold value, the control module 230 may control an input switch 211A to close the first input IN1 and open the second input IN2, and to close the output OUT and open the circulation output COUT. Accordingly, an internal cir-culation path in which the external air passing through the sensor module 220 is intaken to the second input IN2 again, via the gas filter 240.

The gas filter 240 may generate circulating air by filtering gas from the external air passing through the sensor module 220. Due to the gas filter 240, the circulating air may not include a gas component sensed by the sensor module 220, or may include the gas component at a very low concentration. The pump module 210A may supply the circulating air to the sensor module 220 again. Accordingly, unless device failure or noise interference occurs, the magnitude of the sensing signal generated from the circulating air by the sensor module 220 may be smaller than the first threshold value.

When the magnitude of the sensing signal decreases while the second input IN2 and the circulation output COUT are open to supply the circulating air to the sensor module 220, the control module 230 may determine that device failure or noise interference has not occurred, and supply the external air to the sensor module 220 again by closing the second input IN2 and the circulation output COUT and opening the first input IN1 and the output OUT. Then, when the magnitude of the sensing signal increases to (or above) a second threshold value, greater than the first threshold value, the control module 230 may finally output an alarm.

Figure 6:
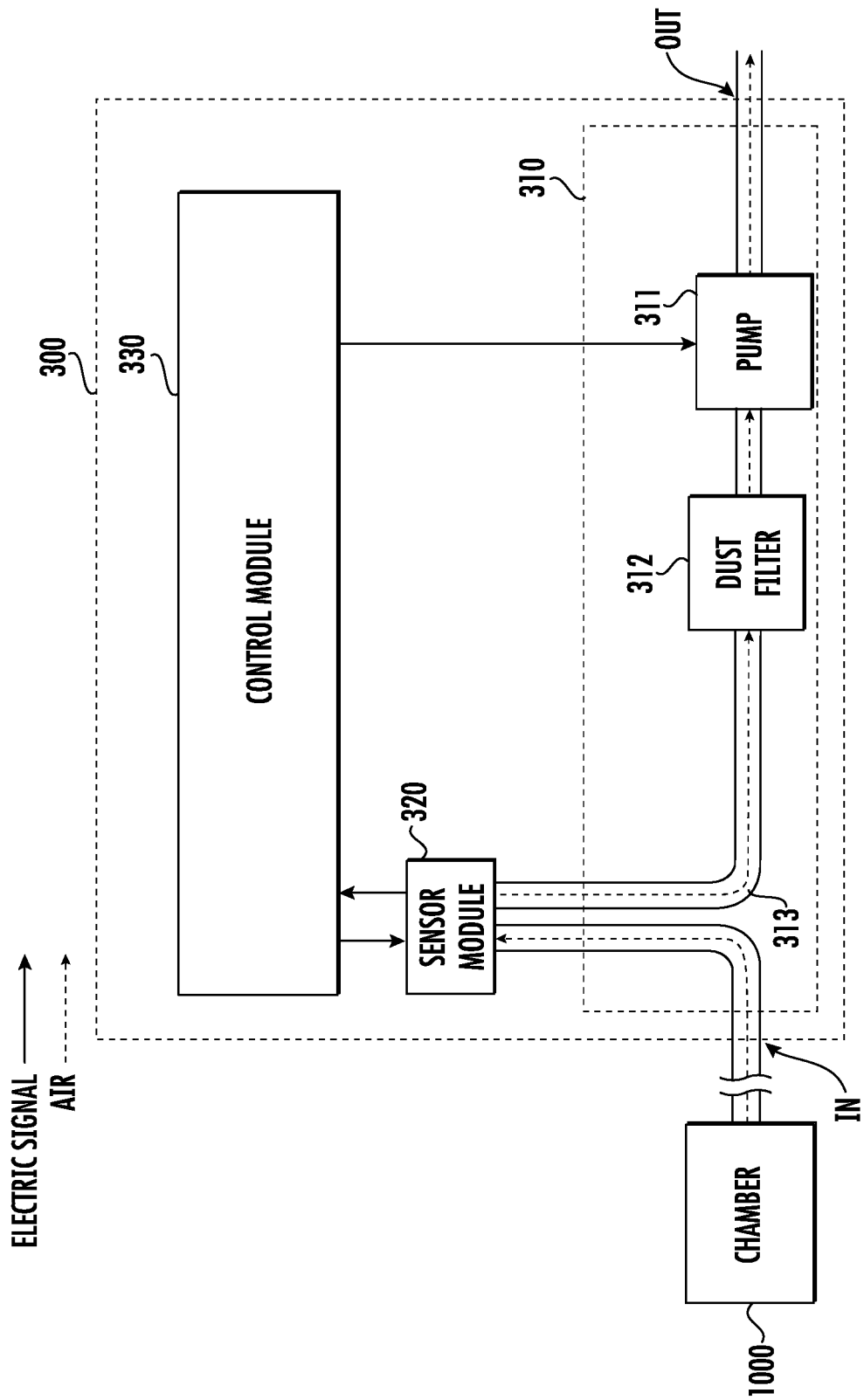
FIGS. 6 to 8 are diagrams provided to illustrate operations of a gas-detecting apparatus according to an example embodiment of the present inventive concept.
Figure 7:
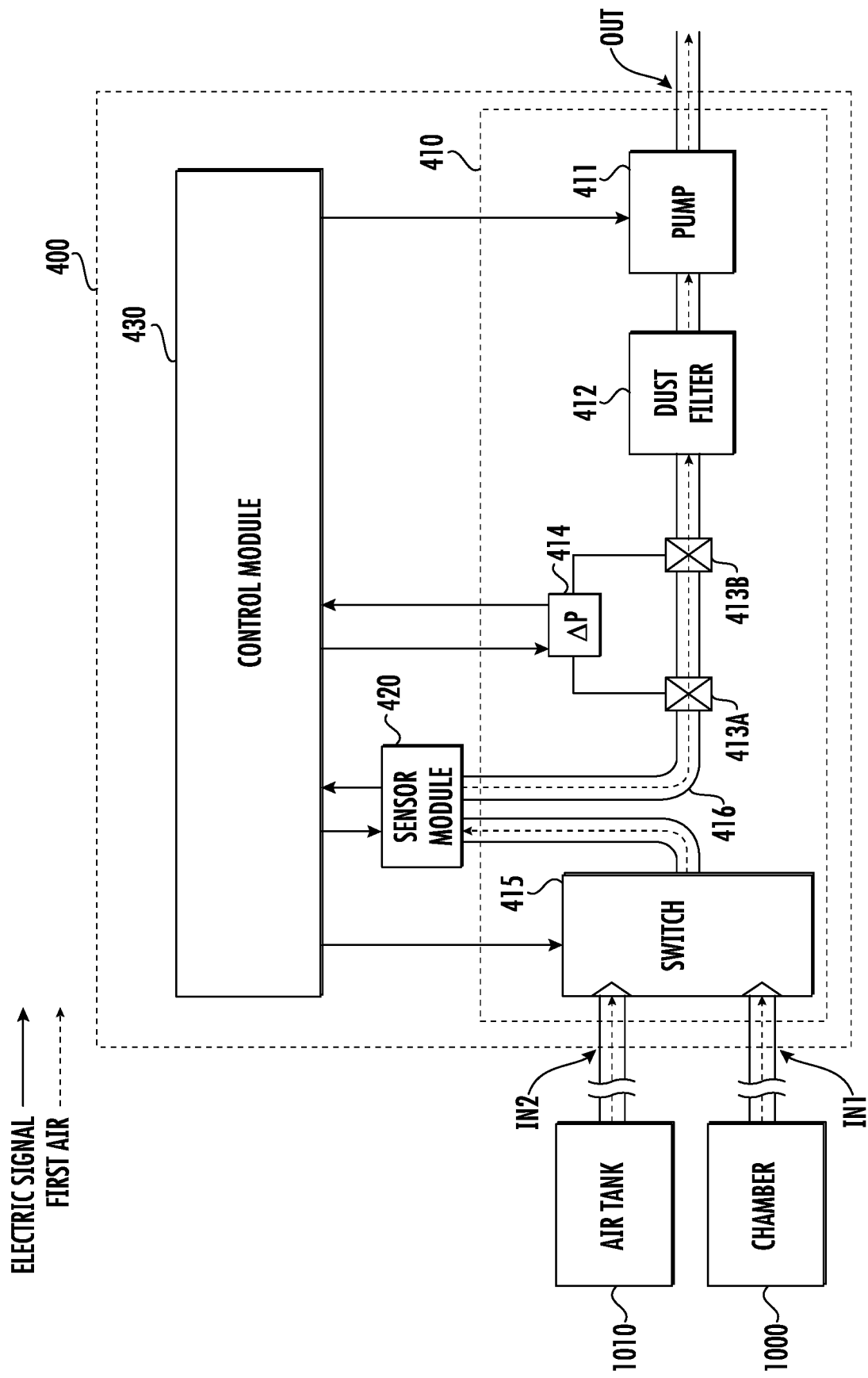
Figure 8:
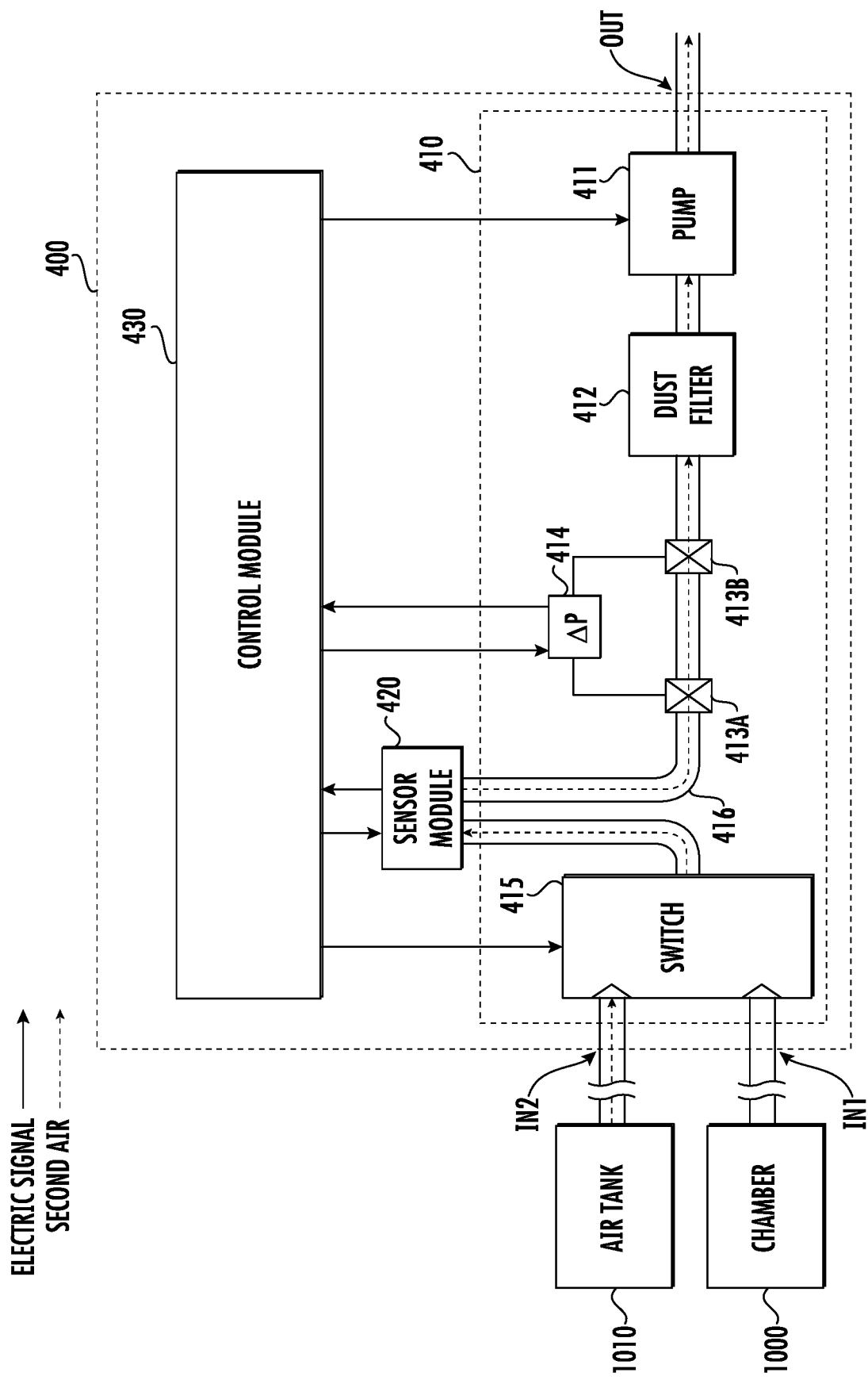

FIGS. 6 to 8 are diagrams provided to illustrate operations of a gas-detecting apparatus according to an example embodiment of the present inventive concept.

First, FIG. 6 is a diagram illustrating a general gas-detecting apparatus 300. Referring to FIG. 6, the gas-detecting apparatus 300 may include a pump module 310, a sensor module 320, and a control module 330, and an input IN of the pump module 310 may be connected to a chamber 1000 in which a gas leak is monitored. The pump module 310 may supply air intaken through the input IN to the sensor module 320, and the air passing through sensor module 320 may be discharged externally through the output OUT.

The pump module 310 may include a pump 311, a dust filter 312, and a microtube 313. The dust filter 312 may remove dust in the air intaken to the pump 311 in order to prevent shortening a lifespan of the pump 311 due to foreign substances. The microtube 313 may provide a path through which the air flows in the gas-detecting apparatus 300. Operations of the pump module 310 and the sensor module 320 may be controlled by the control module 330.

In the gas-detecting apparatus 300 illustrated in FIG. 6, the control module 330 may detect a gas leak in the chamber 1000 and output an alarm, using the magnitude of a sensing signal output by the sensor module 320 in response to gas. However, since the gas-detecting apparatus 300 illustrated in FIG. 6 does not have a means for distinguishing the increase in the magnitude of the sensing signal output from sensor module 320 due to a malfunction of the sensor module 320 or an external electrical noise or radio frequency (RF) noise, from the increase in the magnitude of the sensing signal due to the gas leak, a false alarm may be output. Once the alarm is output, an operator may stop the operations of the chamber 1000 or shut off the gas supplied to the chamber 1000 to check whether or not a gas leak has occurred. The output of the false alarm may result in lowering productivity and increasing the personnel and cost for maintenance and management of the chamber 1000 and the gas-detecting apparatus 300.

FIGS. 7 and 8 are diagrams provided to illustrate operations of a gas-detecting apparatus 400 according to an example embodiment of the present inventive concept, which may solve the problems described above. Referring to FIGS. 7 and 8, the gas-detecting apparatus 400 may include a pump module 410, a sensor module 420, and a control module 430.

The pump module 410 may include a pump 411, a dust filter 412, first and second flow rate sensors 413A and 413B, a pressure computing unit 414, a switch 415, and a microtube 416. The switch 415 may be disposed at an intake portion at which the pump module 410 intakes air, and the pump module 410 may intake air contained in the chamber 1000 through a first input IN1 and air contained in the air tank 1010 through a second input IN2. For example, the chamber 1000 may include a space to be inspected for gas leakage, and the air tank 1010 may include general air that does not include a gas to be inspected. According to another example embodiment, the second input IN2 may be connected to an outdoor space to intake outdoor air.

The first and second flow rate sensors 413A and 413B and the pressure computing unit 414 may be provided to measure pressure of air flowing through the microtube 416. The pressure computing unit 414 may compute the pressure of the air by calculating a difference between a pressure measured by the first flow rate sensor 413A at a first point of the microtube 416 and a pressure measured by the second flow rate sensor 413B at a second point of the microtube 416. The control module 430 may control the amount of the air intaken by the pump module 410 with reference to the pressure difference calculated by the pressure computing unit 414.

First, referring to FIG. 7, the control module 430 may intake first air contained in the chamber 1000 to be supplied to the sensor module 420 by opening the first input IN1 of the switch 415 and closing the second input IN2 of the switch 415. The first air passing through the sensor module 420 may be discharged to the outside through the output OUT. The control module 430 may control the pump module 410 to intake the air contained in the air tank 1010 when the magnitude of a sensing signal output by the sensor module 420 in response to the first air is greater than a first threshold value. This will be described in more detail below with reference to FIG. 8.

When the magnitude of the sensing signal output by the sensor module 420 in response to the first air is greater than the predetermined first threshold value, the control module 430 may control the switch 415 to close the first input IN1 and open the second input IN2, as illustrated in FIG. 8. Accordingly, the first air contained in the chamber 1000 may be no longer intaken to the gas-detecting apparatus 400, and the second air stored in the air tank 1010 may be intaken to the gas-detecting apparatus 400. The control module 430 may open the input IN2 and close the first input IN1 during a predetermined verification time, and the sensor module 420 may receive the second air during the predetermined verification time, as illustrated in FIG. 8.

As described above, the air tank 1010 or the second air intaken from the outside may not include a gas, such as a leaked or sensed gas. Accordingly, the magnitude of the sensing signal output by the sensor module 420 may decrease during the verification time. When the magnitude of the sensing signal sufficiently decreases during the verification time, the control module 430 may determine that the magnitude of the sensing signal has increased to the first threshold value or more due to a gas leak occurring in the chamber 1000 actually, with no other cause, such as a noise or a malfunctioning of the sensor module 420. Accordingly, the control module 430 may determine that there is no possibility that a false alarm has occurred.

When the verification time elapses, the control module 430 may open the first input IN1 and close the second input IN2 again. Here, since there is no other cause, such as a noise or malfunctioning of the sensor module 420, the magnitude of the sensing signal output by the sensor module 420 may increase again. In some example embodiments, the control module 430 may output an alarm when the magnitude of the sensing signal increases again to (or above) the first threshold value, or to (or above) a second threshold value, greater than the first threshold value.

That is, the gas-detecting apparatus 400 according to the example embodiment of the present inventive concept may not output an alarm as soon as the sensing signal output by the sensor module 420 increases. Instead, when the sensing signal increases and exceeds the first threshold value, the gas-detecting apparatus 400 may supply the air that does not include the gas, such as a leaked or sensed gas, to the sensor module 420 by operating the switch 415 during the predetermined verification time. Unless the sensing signal increases due to another cause, such as external noise or malfunctioning of the sensor module 420, the magnitude of the sensing signal may decrease since the air that does not include the gas, such as a leaked or sensed gas, is supplied to the sensor module 420. Unless the magnitude of the sensing signal decreases during the verification time, the control module 430 may determine that the magnitude of the sensing signal has increased due to other causes, such as device failure or noise interference, and the gas-detecting apparatus 400 may output a device maintenance alarm. On the other hand, when the magnitude of the sensing signal decreases during the verification time, the control module 430 may supply air contained in the space in which a gas leak has occurred to the sensor module 420 by operating the switch 415 again, and determine whether to output the alarm by referring to the magnitude of the sensing signal. Accordingly, a false alarm is prevented from being output due to other causes, such as a device failure or a noise inflow.

Figure 9:
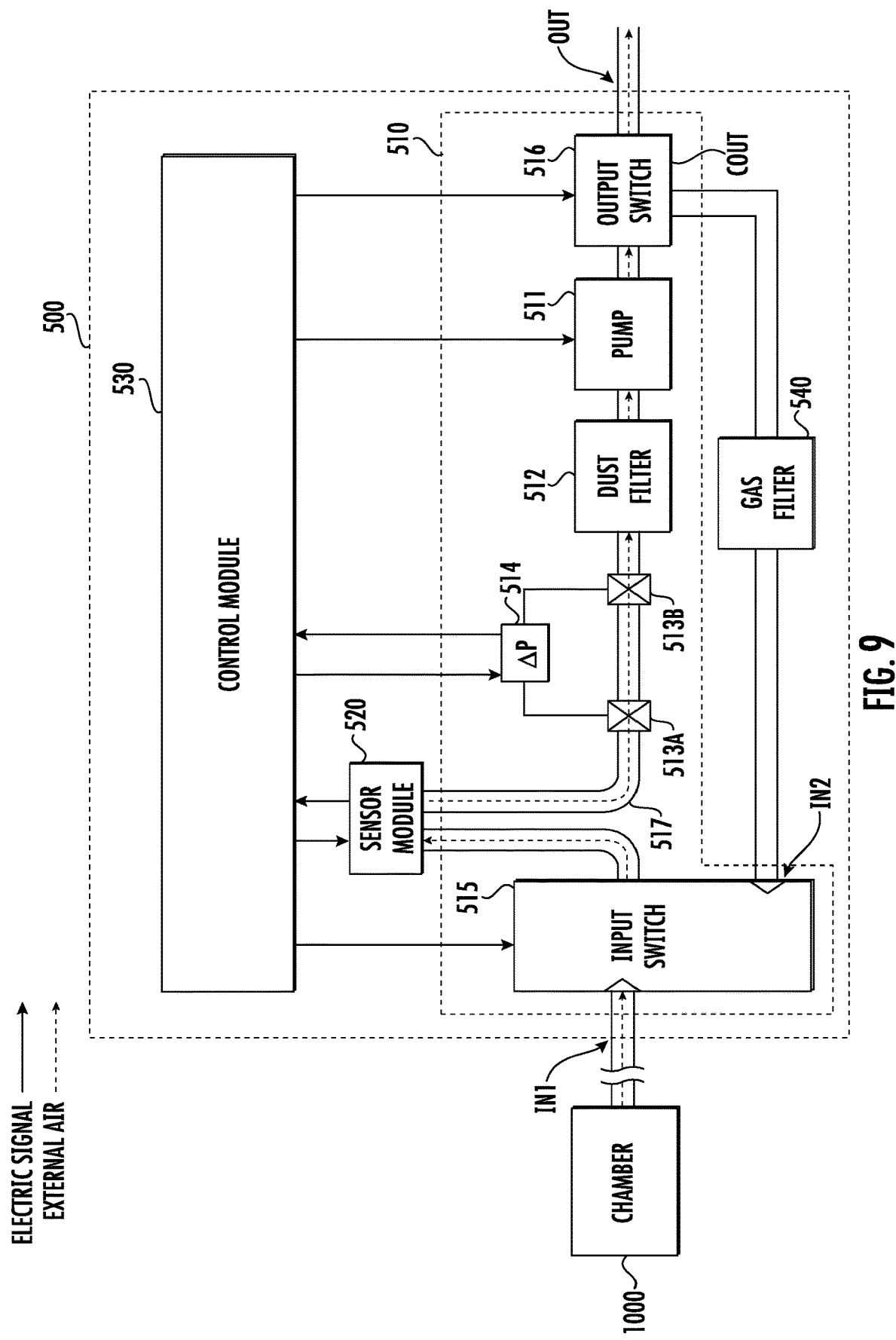
FIGS. 9 and 10 are diagrams provided to illustrate operations of a gas-detecting apparatus according to an example embodiment of the present inventive concept.
Figure 10:
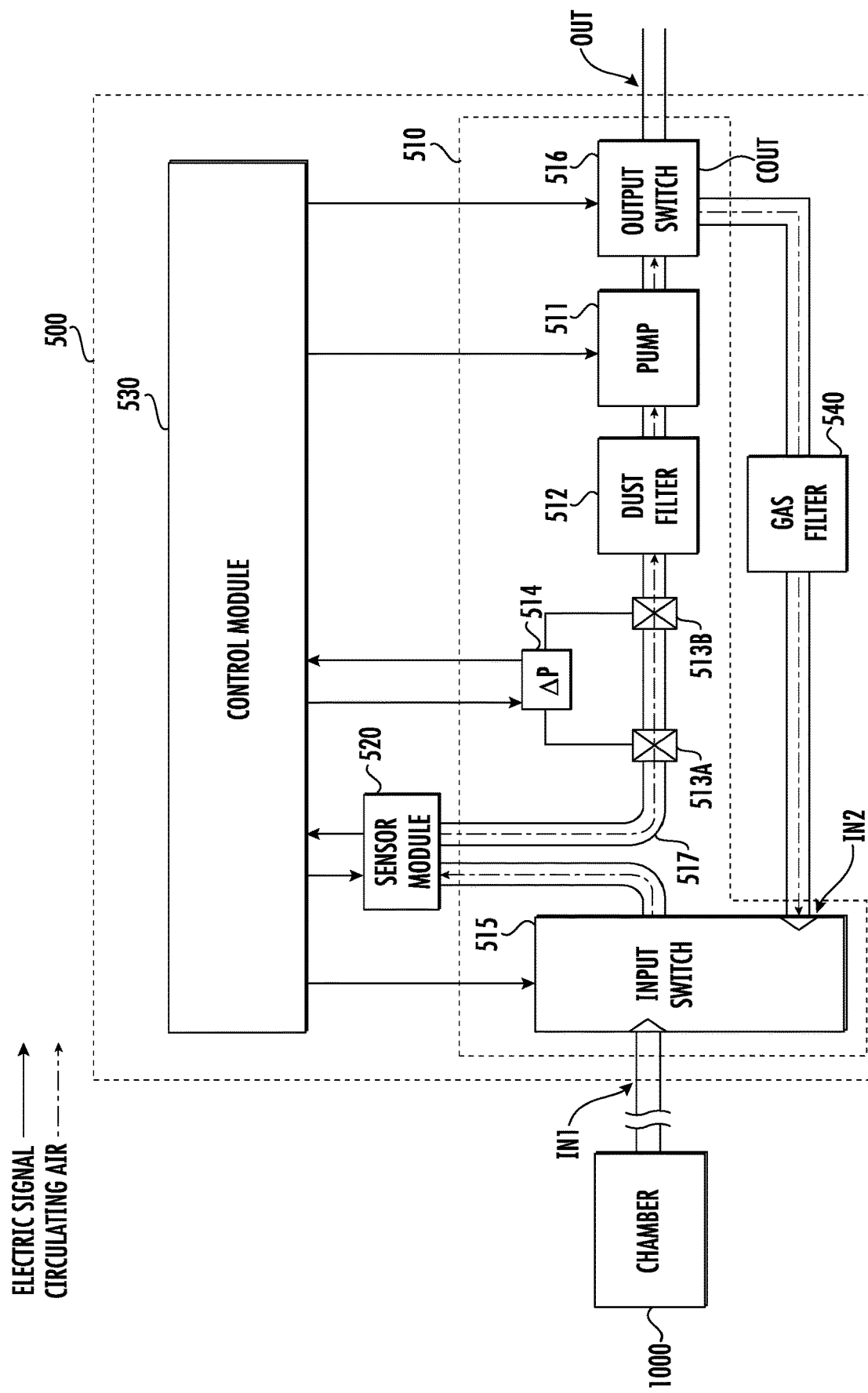

FIGS. 9 and 10 are diagrams provided to illustrate operations of a gas-detecting apparatus according to an example embodiment of the present inventive concept. Referring to FIGS. 9 and 10, a gas-detecting apparatus 500 may include a pump module 510, sensor module 520, control module 530, and a gas filter 540.

The pump module 510 may include a pump 511, a dust filter 512, first and second flow rate sensors 513A and 513B, a pressure computing unit 514, an input switch 515, an output switch 516, and a microtube 517. Among the components, configurations and operations of the pump 511, the dust filter 512, the first and second flow rate sensors 513A and 513B, the pressure computing unit 514, and the microtube 517 may be similar to those described above with reference to FIGS. 7 and 8.

The input switch 515 may be disposed at an intake portion at which the pump module 510 intakes air. The pump module 510 may intake external air from the chamber 1000 through a first input IN1 and circulate air inside the gas-detecting apparatus 500 through a second input IN2. For example, since the chamber 1000 includes a space in which a gas leak is to be detected, the external air may include a gas, such as a leaked or sensed gas, in some cases. On the other hand, since the circulating air is filtered by the gas filter 540 and supplied to the sensor module 520, the circulating air supplied to the sensor module 520 may not include the gas, such as a leaked or sensed gas.

First, referring to FIG. 9, the control module 530 may intake the external air from the chamber 1000 to be supplied to the sensor module 520, by opening the first input IN1 of the input switch 515. The external air passing through the sensor module 520 may be discharged through an output OUT. When the magnitude of a sensing signal output by the sensor module 520 in response to the external air is greater than a first threshold value, the control module 530 may control the pump module 510 to supply the circulating air to the sensor module 520. This will be described in more detail below with reference to FIG. 10.

When the magnitude of the sensing signal output by the sensor module 520 in response to the external air is greater than the predetermined first threshold value, the control module 530 may control the input switch 515 to close the first input IN1 and open the second input IN2, as illustrated in FIG. 10. In addition, the control module 530 may control the output switch 516 to close the output OUT and open the circulation output COUT.

Accordingly, the external air may be no longer supplied to the gas-detecting apparatus 500 from the chamber 1000, and the circulating air already intaken to the gas-detecting apparatus 500 may be filtered by the gas filter 540 to be supplied to the sensor module 520 via the input switch 515. The control module 530 may open the second input IN2 and close the first input IN1, and close the output OUT and open the circulation output COUT, during the predetermined verification time, as illustrated in FIG. 10.

As described above, the circulating air supplied to the sensor module 520 through the gas filter 540 may not include a gas, such as a leaked or sensed gas. Accordingly, the magnitude of the sensing signal output by the sensor module 520 may decrease during the verification time. When the magnitude of the sensing signal sufficiently decreases during the verification time, the control module 530 may determine that the magnitude of the sensing signal has increased to (or above) the first threshold value due to a gas, such as a leaked or sensed gas, leak occurring in the chamber 1000, with no other cause, such as an externally introduced noise or a mal-function of the sensor module 520. Accordingly, the control module 530 may determine that there is no possibility that a false alarm occurs.

When the verification time elapses, the control module 530 may intake the external air again, as illustrated in FIG. 9. That is, the control module 530 may open the first input IN1 of the input switch 515 and close the second input IN2 of the input switch 515, and open the output OUT of the output switch 516 and close the circulation output COUT of the output switch 516. Since there are no other causes, such as a noise inflow or a malfunction of the sensor module 420, the magnitude of the sensing signal output by the sensor module 520 may increase again. In some example embodiments, the control module 530 may output an alarm when the magnitude of the sensing signal increases again to (or above) the first threshold value or to (or above) a second threshold value greater than the first threshold value.

Figure 11:
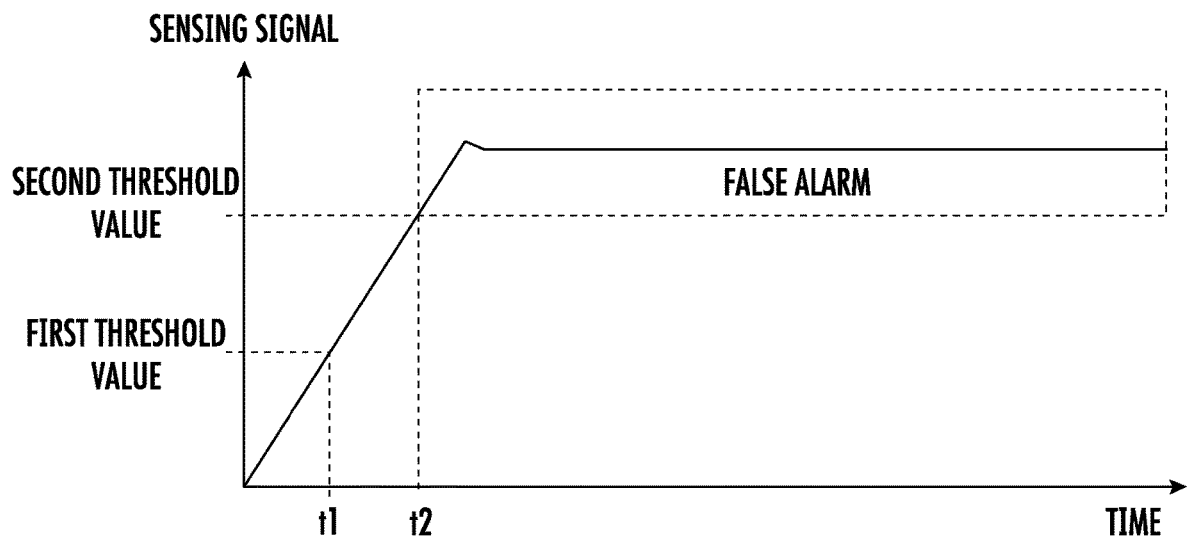
FIGS. 11 and 12 are graphs provided to illustrate operations of a gas-detecting apparatus according to an example embodiment of the present inventive concept.
Figure 12:
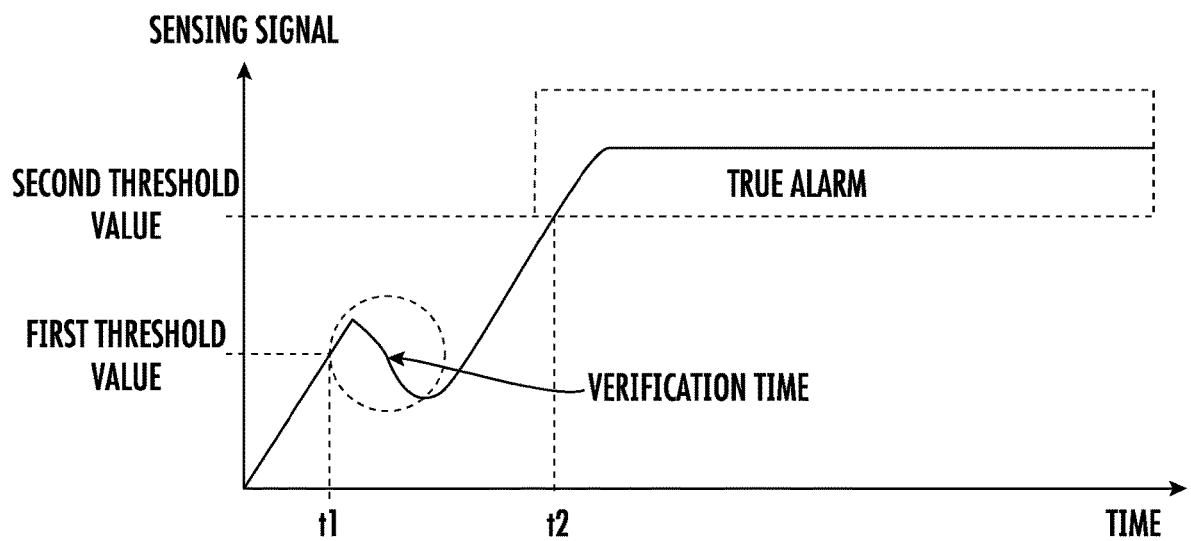

FIGS. 11 and 12 are graphs provided to illustrate operations of a gas-detecting apparatus according to an example embodiment of the present inventive concept.

First, FIG. 11 is a graph provided to illustrate a process of outputting an alarm in a general gas-detecting apparatus. Referring to FIG. 11, the magnitude of a sensing signal output by a sensor module gradually increases to (or above) a first threshold value at a first point in time t1, and to (or above) a second threshold value at a second point in time t2. In the general gas-detecting apparatus, there is no process of verifying whether the increase of the sensing signal occurs due to an actual gas leak or due to an external noise or a malfunction of the sensor module. Accordingly, the magnitude of the sensing signal may be simply compared with the first threshold value and the second threshold value sequentially, and the alarm may be output when the magnitude of the sensing signal exceeds the second threshold value. However, when the magnitude of the sensing signal increases due to externally introduced electromagnetic noise or a malfunction of the sensor module, a false alarm may be output.

FIG. 12 is a graph provided to illustrate a process of outputting an alarm in a gas-detecting apparatus according to an example embodiment of the present inventive concept. Referring to FIG. 12, when the magnitude of a sensing signal output by a sensor module gradually increases to (or above) a first threshold value at a first point in time t1, a predetermined verification time may be set. During the verification time, air that does not include a gas, such as a leaked or sensed gas, may be supplied to the sensor module, as described above with reference to FIGS. 8 and 10. Unless there are other causes, such as an external noise inflow or a malfunction of the sensor module 420, the air that does not include a gas, such as a leaked or sensed gas, may be supplied to the sensor module. Accordingly, the magnitude of the sensing signal may decrease during the verification time, as illustrated in the graph of FIG. 12.

When it is confirmed that the magnitude of the sensing signal decreases during the verification time, the air to be inspected for gas leakage may be supplied to the sensor module 420 again. Accordingly, the magnitude of the sensing signal may increase again as illustrated in FIG. 12, and the gas-detecting apparatus may output an alarm at a second point in time t2 at which the magnitude of the sensing signal increases to (or above) a second threshold value. According to the example embodiments of the present inventive concept, the air that does not include a gas, such as a leaked or sensed gas, may be intentionally supplied to the sensor module to check whether or not the magnitude of the sensing signal decreases during the verification time. Accordingly, a gas-detecting apparatus may be implemented to output an alarm only when a gas leak has actually occurred, with no other causes, such as an external noise inflow or a malfunction of a sensor module.

As set forth above, when a gas leak is detected due to a sensing signal generated in response to gas, such as a leaked or sensed gas, a gas-detecting apparatus according to the example embodiments of the present inventive concept may intake air that does not include the gas, such as a leaked or sensed gas, for a certain period of time, and determine whether or not the magnitude of the sensing signal decreases. Accordingly, it can be prevented that a false alarm is output due to a malfunction of a sensor, a noise caused by an electric signal or RF signal, or the like. Therefore, smooth operations of a chamber, a gas pipe, or the like connected to the gas-detecting apparatus can be ensured.

While example embodiments have been shown and described above, it will be apparent to those skilled in the art that modifications and variations could be made without departing from the scope of the present invention as defined by the appended claims.

The invention claimed is:

1. A gas-detecting apparatus, comprising:
a pump module connected to a first input and a second input to intake air;
a sensor module including at least one unit sensor configured to output a sensing signal in response to gas present in the air; and
a control module configured to detect the gas using the sensing signal,
wherein when gas is detected in first air introduced through the first input, the control module controls the pump module to intake second air by opening the second input during a predetermined verification time, and
when the sensing signal decreases during the predetermined verification time, the control module determines that gas is detected.

2. The gas-detecting apparatus of claim 1, wherein the control module opens the second input to intake the second air when the sensing signal output by the sensor module in response to the first air exceeds a predetermined first threshold value.

3. The gas-detecting apparatus of claim 2, wherein when the sensing signal decreases during the verification time, the control module opens the first input and closes the second input to intake the first air again after the verification time, and
when the sensing signal exceeds the first threshold value after the verification time, the control module determines that gas is detected, and outputs an alarm.

4. The gas-detecting apparatus of claim 3, wherein the control module outputs the alarm when the sensing signal exceeds a second threshold value greater than the first threshold value.

5. The gas-detecting apparatus of claim 1, further comprising a switch configured to determine whether to open or close the first input and the second input.

6. The gas-detecting apparatus of claim 5, wherein the control module controls the switch to selectively open and close the first input and the second input.

7. The gas-detecting apparatus of claim 1, wherein the pump module includes a microtube configured to provide a path of the first air and the second air, and a pressure measuring unit connected to the microtube and measuring pressures of the first air and the second air.

8. The gas-detecting apparatus of claim 7, wherein the pressure measuring unit includes a first flow rate sensor connected to a first point of the microtube, a second flow rate sensor connected to a second point of the microtube, different from the first point, and a pressure computing part configured to calculate the pressures of the first air and the second air based on values respectively measured by the first flow rate sensor and the second flow rate sensor.

9. The gas-detecting apparatus of claim 1, wherein the first input is connected to a work space in which an operation using the gas is performed, and the second input is connected to at least one of an external space different from the work space and a separate air tank.

10. A gas-detecting apparatus, comprising:
a sensor module including at least one unit sensor configured to output a sensing signal in response to gas;
a pump module configured to supply at least one of external air, having been intaken, through a first input and circulating air intaken through a second input to the sensor module;
a control module configured to detect the gas using the sensing signal; and
a gas filter configured to generate the circulating air by filtering the external air passing through the sensor module,
wherein when gas is detected in the external air, the control module supplies the circulating air to the sensor module by closing the first input and opening the second input, and
when a concentration of gas detected in the circulating air is lower than a concentration of gas detected in the external air, the control module determines that that gas is detected.

11. The gas-detecting apparatus of claim 10, wherein when the concentration of gas detected in the external air exceeds a predetermined first threshold value, the control module closes the first input and opens the second input.

12. The gas-detecting apparatus of claim 11, wherein when the concentration of gas detected in the circulating air is lower than the first threshold value, the control module supplies the external air to the sensor module by opening the first input and closing the second input, and
when the concentration of gas detected in the external air is higher than a second threshold value greater than the first threshold value, the control module determines that gas is detected.

13. The gas-detecting apparatus of claim 10, wherein the pump module determines whether the first input and the second input are to be opened or closed, and includes an input switch connected to an input of the sensor module and an output switch connected to an output of the pump module.

14. The gas-detecting apparatus of claim 13, wherein the input switch and the output switch include valves.

15. The gas-detecting apparatus of claim 13, wherein when gas is detected in the external air, the control module controls the output switch to introduce the external air to the gas filter.

16. The gas-detecting apparatus of claim 10, wherein the first input is connected to a work space in which operation using the gas is performed.

17. The gas-detecting apparatus of claim 10, wherein the pump module includes a microtube configured to provide a path for the air, and a pressure measuring unit connected to the microtube and measuring a pressure of the air.

18. The gas-detecting apparatus of claim 17, wherein the pressure measuring unit includes a first flow rate sensor connected to a first point of the microtube, a second flow rate sensor connected to a second point of the microtube, different from the first point, and a pressure computing part configured to calculate the pressure of the air based on values respectively detected by the first flow rate sensor and the second flow rate sensor.

19. A gas-detecting apparatus, comprising:
a pump module configured to intake air;
a sensor module configured to detect gas present in the air at a first point in time and a second point in time coming after the first point in time and output a sensing signal; and
a control module configured to determine whether or not to output an alarm by setting a first threshold value and a second threshold value greater than the first threshold value, comparing the sensing signal with the first threshold value at the first point in time, and comparing the sensing signal with the second threshold value at the second point in time,
wherein the control module outputs the alarm when the sensing signal decreases during a predetermined verification time defined between the first point in time and the second point in time.

20. The gas-detecting apparatus of claim 19, wherein the control module controls the pump module to intake air in which the gas is not included, during the verification time.

* * * * *